(12) United States Patent
Radl et al.

(10) Patent No.: US 10,888,446 B2
(45) Date of Patent: Jan. 12, 2021

(54) SYSTEMS AND METHODS FOR PERFORMING BARIATRIC SURGERY

(71) Applicant: Boehringer Technologies, LP, Phoenixville, PA (US)

(72) Inventors: Christopher L. Radl, Malvern, PA (US); Trevor Smith, Phoenixville, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 589 days.

(21) Appl. No.: 15/730,332

(22) Filed: Oct. 11, 2017

(65) Prior Publication Data

US 2018/0028340 A1 Feb. 1, 2018

Related U.S. Application Data

(63) Continuation of application No. 14/073,464, filed on Nov. 6, 2013, now Pat. No. 9,808,368.

(Continued)

(51) Int. Cl.
*A61F 5/00* (2006.01)
*A61B 17/072* (2006.01)
(Continued)

(52) U.S. Cl.
CPC ...... *A61F 5/0089* (2013.01); *A61B 17/07207* (2013.01); *A61B 2017/00818* (2013.01);
(Continued)

(58) Field of Classification Search
CPC ........ A61B 17/07207; A61B 2017/306; A61B 2017/00818; A61B 2017/320052;
(Continued)

(56) References Cited

U.S. PATENT DOCUMENTS 3,565,076 A * 2/1971 Kadan ................. A61M 1/0031
604/67
3,888,249 A * 6/1975 Spencer ............ A61M 25/0021
604/247

(Continued)

FOREIGN PATENT DOCUMENTS

| WO | 2011161148 A1 | 12/2011 |
| WO | 2012138737 A1 | 10/2012 |
| WO | 2012141679 A1 | 10/2012 |

OTHER PUBLICATIONS

Ethicon Endo-Surgery, Gastric Calibration Tube—Instructions for Use, 2012, pp. 1-8.

(Continued)

*Primary Examiner* — Daniel L Cerioni
*Assistant Examiner* — Raymond P Dulman
(74) *Attorney, Agent, or Firm* — Caesar Rivise, PC

(57) ABSTRACT

Systems and methods for effecting bariatric procedures are disclosed. Each system includes an instrument, a control valve and, optionally, a suction controller. The instrument is in the form of an elongated, flexible sizing tube having a distal end portion including a plurality of apertures. The control valve enables suction to be applied to the patient's stomach via the apertures to drain gastric fluids and to bring adjacent portions of the patient's stomach into engagement the sizing tube to provide a visually perceptible delineation line along which a portion of the stomach may be resected, sealed and tested.

14 Claims, 5 Drawing Sheets

Related U.S. Application Data

(60) Provisional application No. 61/837,908, filed on Jun. 21, 2013, provisional application No. 61/777,432, filed on Mar. 12, 2013, provisional application No. 61/731,200, filed on Nov. 29, 2012.

(51) Int. Cl.
*A61M 25/00* (2006.01)
*A61B 17/30* (2006.01)
*A61B 17/32* (2006.01)
*A61B 17/00* (2006.01)
*A61J 15/00* (2006.01)

(52) U.S. Cl.
CPC ............ *A61B 2017/306* (2013.01); *A61B 2017/320052* (2013.01); *A61J 15/0003* (2013.01); *A61M 25/007* (2013.01)

(58) Field of Classification Search
CPC .. A61F 5/0089; A61J 15/0003; A61M 25/007; A61M 1/0031; A61M 1/0037; A61M 1/0049; A61M 1/005; A61M 1/0052; A61M 1/0058; A61M 1/0066; A61M 1/0068; A61M 1/0072; A61M 1/0074; A61M 1/1037; A61M 1/1081
USPC ........................................................ 600/593
See application file for complete search history.

(56) References Cited

U.S. PATENT DOCUMENTS

| | | | |
|---|---|---|---|
| 5,382,231 A | 1/1995 | Shlain | |
| 5,405,316 A * | 4/1995 | Magram | A61M 25/007 604/175 |
| 5,992,239 A | 11/1999 | Boehringer et al. | |
| 6,024,120 A * | 2/2000 | Yam | A61M 1/0031 128/204.26 |
| 7,438,705 B2 * | 10/2008 | Karpowicz | A61M 1/0031 604/313 |
| 7,686,785 B2 | 3/2010 | Boehringer et al. | |
| 7,857,806 B2 | 12/2010 | Karpowicz et al. | |
| 7,896,894 B2 | 3/2011 | Ortiz et al. | |
| 8,211,128 B1 | 7/2012 | Facundus et al. | |
| 8,663,149 B2 | 3/2014 | Gagner et al. | |
| 2002/0183768 A1 | 12/2002 | Deem et al. | |
| 2003/0120265 A1 | 6/2003 | Deem et al. | |
| 2004/0133226 A1 * | 7/2004 | Buckman | A61M 27/00 606/167 |
| 2005/0113798 A1 * | 5/2005 | Slater | A61M 25/10 604/508 |
| 2005/0251158 A1 | 11/2005 | Saadat et al. | |
| 2005/0261663 A1 | 11/2005 | Patterson et al. | |
| 2006/0025727 A1 | 2/2006 | Boehringer et al. | |
| 2006/0106288 A1 | 5/2006 | Roth et al. | |
| 2006/0200191 A1 * | 9/2006 | Zadno-Azizi | A61B 17/12136 606/200 |
| 2007/0032702 A1 | 2/2007 | Ortiz | |
| 2007/0032800 A1 | 2/2007 | Ortiz et al. | |
| 2007/0175488 A1 | 8/2007 | Cox et al. | |
| 2008/0015504 A1 | 1/2008 | Boehringer et al. | |
| 2008/0249404 A1 | 10/2008 | Mikkaichi et al. | |
| 2008/0275473 A1 | 11/2008 | Filipi et al. | |
| 2009/0012544 A1 | 1/2009 | Thompson et al. | |
| 2009/0275937 A1 | 11/2009 | Stokes et al. | |
| 2009/0275960 A1 | 11/2009 | Provenza et al. | |
| 2010/0191264 A1 | 7/2010 | Kassab et al. | |
| 2011/0178454 A1 | 7/2011 | Gagner et al. | |
| 2011/0184338 A1 * | 7/2011 | McKay | A61M 25/003 604/28 |
| 2011/0288576 A1 | 11/2011 | Hoffman | |
| 2011/0295286 A1 | 12/2011 | Harris et al. | |
| 2012/0016393 A1 | 1/2012 | Murray et al. | |
| 2012/0123463 A1 | 5/2012 | Jacobs | |
| 2012/0238972 A1 | 9/2012 | Karpowicz et al. | |
| 2012/0277525 A1 | 11/2012 | O'Dea | |
| 2013/0066297 A1 * | 3/2013 | Shtul | A61M 3/0208 604/514 |
| 2013/0085438 A1 | 4/2013 | MacMeans et al. | |
| 2013/0131440 A1 | 5/2013 | Gabriel | |
| 2013/0165774 A1 | 6/2013 | Nocca | |
| 2013/0178698 A1 | 7/2013 | Bender et al. | |
| 2013/0178877 A1 | 7/2013 | Bender et al. | |
| 2014/0018722 A1 | 1/2014 | Scott et al. | |
| 2014/0039278 A1 | 2/2014 | Birk | |
| 2014/0073858 A1 | 3/2014 | Sherwinter | |
| 2014/0081176 A1 | 3/2014 | Hassan | |
| 2014/0107698 A1 | 4/2014 | Inge | |
| 2014/0114121 A1 | 4/2014 | Trivedi | |
| 2014/0155918 A1 | 6/2014 | Gagner et al. | |
| 2014/0276991 A1 | 9/2014 | Schauer | |
| 2015/0209239 A1 * | 7/2015 | Salvino | A61J 15/0069 604/516 |
| 2016/0256170 A1 * | 9/2016 | Busold | A61M 25/0067 |
| 2019/0083732 A1 * | 3/2019 | Vadivelu | A61M 16/0415 |

OTHER PUBLICATIONS

Cook Surgical Products—Gastric Sizing Balloon Catheter product brochure, C-GSB905, 2005, pp. 1-4.

International Search Report for PCT/US2013/070073 dated Feb. 11, 2014.

Boehringer Laboratories, Inc. "7700 Series Suction Regulator Technical Manual and Operating and Maintenance Instructions." (2004): 1-14.

* cited by examiner

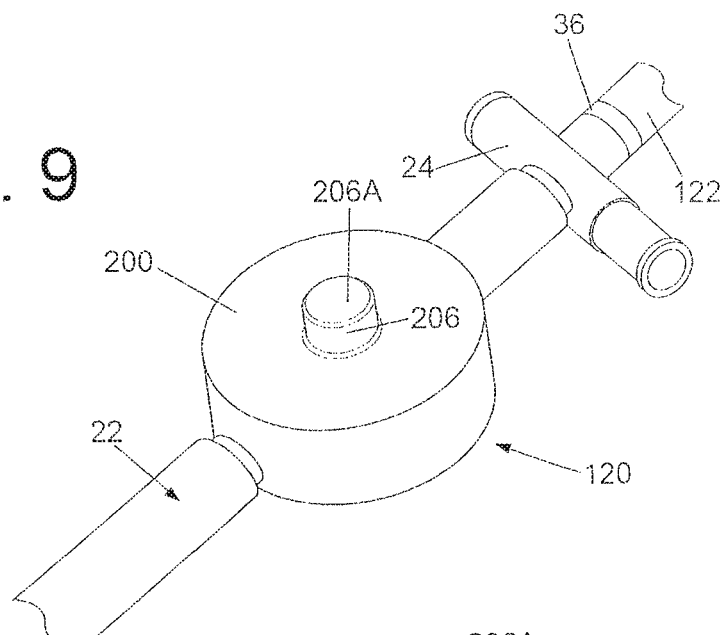
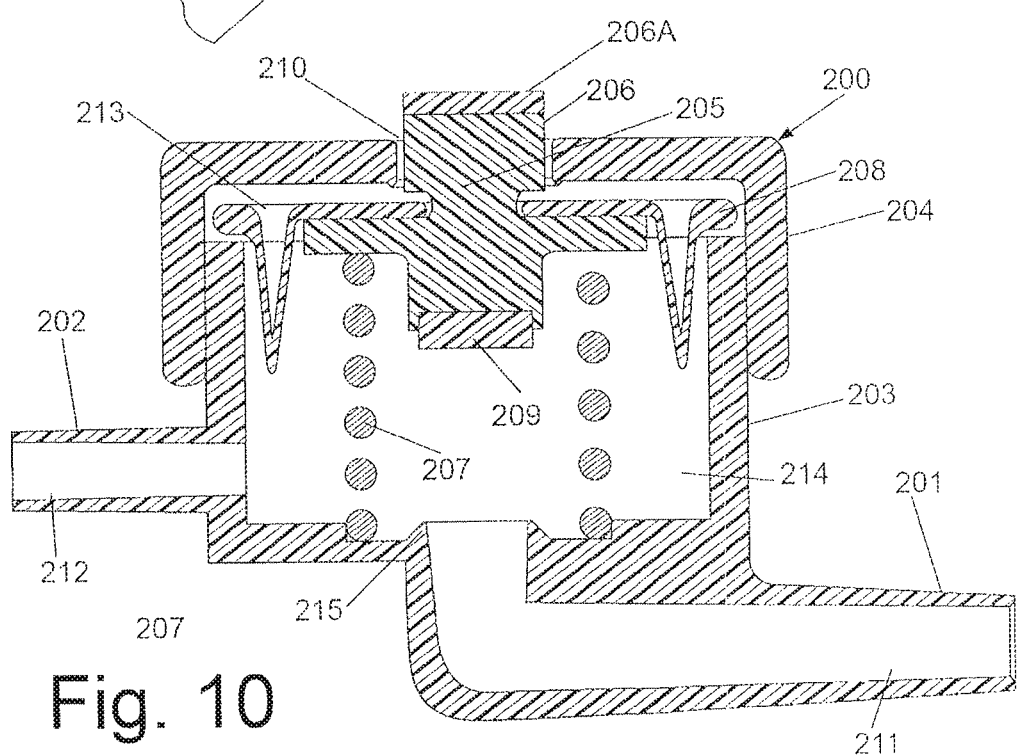

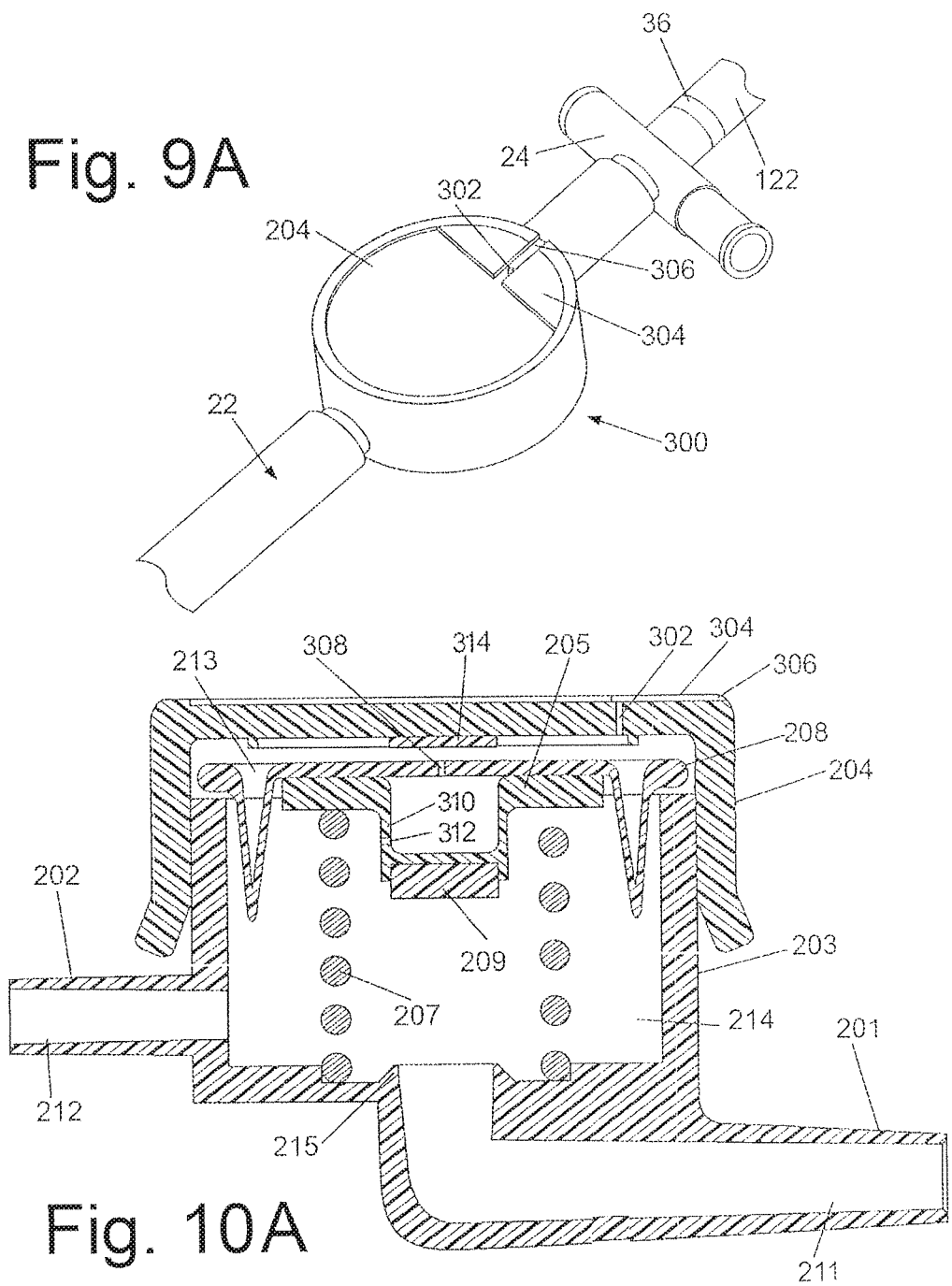

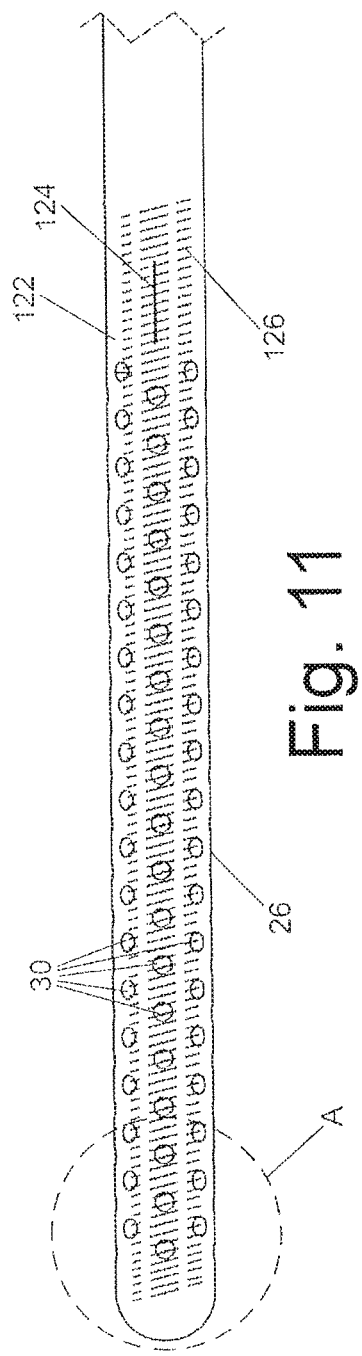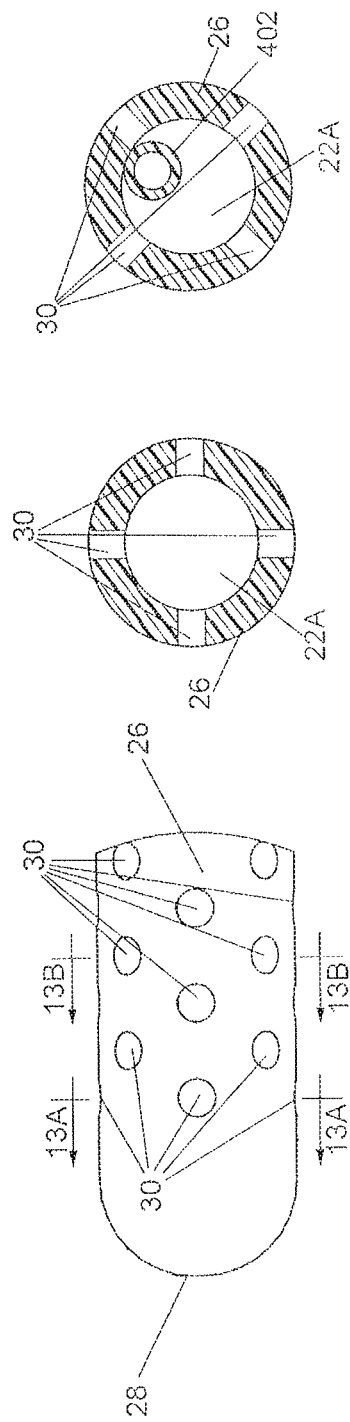

SYSTEMS AND METHODS FOR PERFORMING BARIATRIC SURGERY

CROSS REFERENCE TO RELATED APPLICATIONS

This application is a continuation of application Ser. No. 14/073,464, filed on Nov. 6, 2013, entitled Methods For Performing Bariatric Surgery Using Gastric Sizing Systems And Instruments, which in turn claims priority from provisional applications: Ser. No. 61/837,908, filed on Jun. 21, 2013, entitled Gastric Sizing Instruments With Anti-Blocking Feature And Methods Of Use In Bariatric Surgery; Ser. No. 61/777,432, filed on Mar. 12, 2013, entitled Gastric Sizing Device And Method Of Use In Bariatric Surgery; and Ser. No. 61/731,200, filed on Nov. 29, 2012, entitled Gastric Sizing Device And Method Of Use In Bariatric Surgery, all of which applications are assigned to the same assignee as the subject invention and whose disclosures are specifically incorporated by reference herein.

FIELD OF THE INVENTION

This invention relates generally to systems and medical instruments arranged for introduction into the stomach of a patient and more particularly to systems including gastric sizing instruments for effecting bariatric metabolic surgeries, such as a Sleeve Gastrectomy.

BACKGROUND OF THE INVENTION

As is known, bariatric surgery (frequently referred to as weight-loss surgery) includes a variety of procedures performed on people who are morbidly obese. One commonly performed procedure is referred to as a sleeve gastrectomy and entails reducing the size of the stomach through removal of a portion of it. In particular, a large portion of the stomach following the stomach's lesser curve is resected, typically laparoscopically, and the open edges of the remaining portion of the patient's stomach are then attached, e.g., stapled, together to form a tube or "sleeve", leaving the patient with a stomach which is substantially smaller, e.g., about 25% of its original size.

Heretofore, sleeve gastrectomies have been accomplished by introducing a Bougie (esophageal dilator) of a specific size into the stomach via the esophagus so that it is disposed along the lesser curvature of the stomach. When in place, it provides a guide where the stomach is to be resected. The resection is typically accomplished via the use of a cutting stapler.

While the instruments used in the prior art are generally suitable for their intended purposes, they nevertheless leave much to be desired from the standpoint of integrating many of the various functions that need to be performed into one device for performing those functions. United States Published Application 2011/0288576 A1 discloses a Bougie gastric tube which is arranged to perform the function of ensuring patency of the esophagus and that the integrity of the stomach's attachment to the esophagus, serving as a guide for the amount of stomach that can be removed and testing the integrity of the suture or staple line.

While the Bougie tube disclosed in the forgoing application may be generally suitable for its intended purpose, it still leaves much to be desired from the standpoints of integrating all of the procedures necessary for a sleeve gastrectomy into one device and for providing a good visual indication of the line along which the stomach is to be resected to enable such action to be readily accomplished and to provide an instrument which is resistant to becoming stuck in the stomach.

Thus, a need exists for systems and instrument which address those needs. The subject invention does that.

SUMMARY OF THE INVENTION

In accordance with one aspect of this invention a system for sizing the stomach of a patient for a bariatric procedure is provided. The system comprises a sizing tube that is sufficiently flexible to be introduced through the esophagus into the stomach of the patient so that a portion of said sizing tube is disposed along a lesser curvature of the patient's stomach. The sizing tube comprises an elongated tubular member having a hollow interior, a longitudinal axis, a distal free end and a proximal end portion. The tubular member comprises a sidewall and a large plurality of apertures disposed in an array extending about the periphery of the sidewall from a point adjacent the free end for a portion of the length of the sizing tube that is disposed along the lesser curvature of the patient's stomach. The plurality of apertures is in fluid communication with the hollow interior of the sizing tube. The sizing tube is arranged to be coupled to a source of suction, whereupon controlled suction is applied to the hollow interior of the sizing tube to effect the drainage of gastric fluids from the patient's stomach through at least some of the apertures of the array of apertures and to bring adjacent portions of the patient's stomach into close engagement with portions of the periphery of the sizing tube at the location of the array of apertures to enable the patient's stomach to be sized. The plurality of apertures extends along a sufficient portion of the length of the sizing tube to hold the sizing tube in place when the controlled suction is applied.

In accordance with one preferred aspect of the invention the sidewall of the sizing tube includes at least one one-way valve which is automatically closed when suction is applied to the interior of the sizing tube and which is openable to enable a fluid to be passed therethrough from the interior of the sizing tube into the stomach of the patient to prevent the sizing tube from becoming stuck in the patient's stomach.

In accordance with another preferred aspect of the invention the system additionally comprises a control valve connected to the sizing tube at the proximal end portion thereof. The control valve is arranged to be connected to a source of suction and when opened provides suction from the source of suction to the hollow interior of the sizing tube. When closed, the control valve provides a vent to the ambient atmosphere to preclude suction from being applied to the distal end of the sizing tube and to enable any residual suction or pressure within the patient's stomach to equilibrate to ambient atmospheric levels.

In accordance with another preferred aspect of the invention the system additionally comprises a suction controller for controlling the level of suction provided to said sizing tube and an indicator for indicating the level of suction provided to the sizing tube.

In accordance with another preferred aspect of the invention the system additionally comprises a bulb arranged to be connected to the control valve, whereupon when the bulb is connected thereto and the control valve is opened a fluid can be pumped from the bulb into the sizing tube and out through the plurality of apertures into the patient's stomach.

In accordance with another preferred aspect of the invention the sizing tube has an outside diameter of at least 0.375 inch and the array of apertures comprises a first region and a second region. The first region is at least approximately 2 inches in length measured along the longitudinal axis and the aggregate area of the apertures in the first region is at least 10% of the area of the first region. The second region is at least approximately 3 inches in length measured along the longitudinal axis and located proximally of the first region. The aggregate area of the apertures in the second region is at least 2% of the area of the second region.

In accordance with another aspect of the invention there is provided a system for use in a patient's stomach for accomplishing a bariatric procedure. The system comprises a sizing tube and a controller. The sizing tube comprises a hollow flexible member having a sidewall including a plurality of apertures therein. The suction controller is arranged to be connected to a source of suction to provide suction to the sizing tube, whereupon a suction force of 0.05 to 200 pounds is applied within the patient's stomach when the system is connected to the source of suction.

In accordance with another aspect of the invention there is provided a system for use in a patient's stomach for accomplishing a bariatric procedure. The system comprises a sizing tube and a controller. The sizing tube comprises a hollow flexible member having a sidewall including a plurality of apertures therein. The suction controller is arranged to be connected to a source of suction to provide suction to the sizing tube, wherein the sizing tube applies a suction force per unit length within the patient's stomach at the location of the apertures when the suction is applied to the sizing tube, with the suction force per unit length being in a range of 0.02 to 21 pounds per inch.

The subject invention also entails methods of sizing the stomach of a patient for a bariatric procedure. The method basically comprises introducing a sizing tube into the stomach of the patient through the patient's esophagus so that a portion of said sizing tube is disposed along the lesser curvature of the patient's stomach. The sizing tube comprises an elongated member having a hollow interior, a distal end portion and a proximal end portion, with the distal end portion having a predetermined outside diameter and a plurality of apertures disposed in an array extending about the periphery of the sizing tube for a portion of the length of the sizing tube that is disposed within the patient's stomach. The plurality of apertures is in fluid communication with the hollow interior of said sizing tube. The sizing tube is connected to a source of suction, whereupon controlled suction is applied from the source of suction via the array of apertures to bring adjacent portions of the patient's stomach into close engagement with portions of the periphery of the sizing tube at the location of the array of apertures and to hold those portions of the patient's stomach in such engagement with the sizing tube to thereby provide a visually perceptible delineation line to enable the patient's stomach to be sized. The plurality of apertures extends along a sufficient portion of the length of the sizing tube to hold the sizing tube in place when the controlled suction is applied.

In accordance with one preferred aspect of the method of this invention if during the application of suction to the patient's stomach via the sizing tube the patient's stomach becomes folded with at least one fold obscuring or interfering with the visualization of the visually perceptible delineation line, the method comprises additional steps. They are discontinuing the application of suction to the patient's stomach via the sizing tube and introducing a fluid into the patient's stomach through the sizing tube to thereby remove the at least one fold. Suction can then be reapplied to the patient's stomach to hold those portions of the patient's stomach in such engagement with the sizing tube to thereby provide the visually perceptible delineation line.

In accordance with another preferred aspect of this invention the method entails resecting the patient's stomach along a resection line. The resection line is located adjacent the delineation line, whereupon when the patient's stomach is resected along the resection line that action creates a residual portion of the patient's stomach. The residual portion of the patient's stomach can then be sealed along the resection line to produce a seal line.

In accordance with another preferred aspect of this invention the method entails producing the seal line at least 0.5 cm from the delineation line on the opposite side of the delineation line from the position of the sizing tube in the vicinity of the gastric esophageal junction (GEJ) and the Angle of HIS.

In accordance with another preferred aspect of this invention the method entails producing the seal line at least 0.5 cm from the delineation line on the opposite side of the delineation line from the position of the sizing tube in the vicinity of the incisura angularis.

In accordance with another preferred aspect of this invention the method entails comprising testing the seal line for leakage, e.g., a fluid is introduced into the residual portion of the patient's stomach to provide an observable indication of leakage.

In accordance with another preferred aspect of this invention the method entails monitoring the level of suction in the distal portion of the sizing tube.

In accordance with another preferred aspect of this invention the method entails withdrawing secretions of the patient's stomach that may have gained ingress into the hollow interior of the sizing tube while the sizing tube is in place in the patient's stomach.

In accordance with another preferred aspect of this invention the method entails monitoring fluid flow through the sizing tube.

In accordance with another aspect of this invention the method entails sizing the stomach of a patient for a bariatric procedure by introducing a sizing tube into the patient's stomach. The sizing tube comprises an elongated member having a distal end portion including a large plurality of apertures disposed in an array extending about the periphery of the sizing tube. Suction is applied to the sizing tube to decompress the patient's stomach. At least one procedure is performed on the patient's stomach while maintaining the sizing tube in the patient's stomach, with or without suction applied thereto. The sizing tube is positioned along the lesser curvature of the patient's stomach. Regulated suction is applied to the patient's stomach via the sizing tube while the sizing tube is in position along the lesser curvature of the patient's stomach to provide a visually perceptible delineation line along the sizing tube and to hold the sizing tube in position. The patient's stomach is resected along a line using the delineation line as a guide. The patient's stomach is closed along a sealing line using the delineation line as a guide. In accordance with one preferred aspect of this method the application of regulated suction to the patient's stomach results in a suction force of 0.05 to 200 pounds within the patient's stomach. In accordance with another preferred aspect of this method the application of regulated suction to the patient's stomach applies a suction force per unit length within the patient's stomach at the location of the apertures, with the suction force per unit length being in a range of 0.02 to 21 pounds per inch.

In accordance with another aspect of this invention the method entails sizing the stomach of a patient for a bariatric procedure by introducing a sizing tube into the patient's stomach. The sizing tube comprises an elongated member having a distal end portion including a large plurality of apertures disposed in an array extending about the periphery of the sizing tube. The sizing tube is positioned along the lesser curvature of the patient's stomach. Regulated suction is applied to the patient's stomach via the sizing tube while the sizing tube is in position along the lesser curvature of the patient's stomach to provide a visually perceptible delineation line along the sizing tube and to hold the sizing tube in position. The patient's stomach is resected along a line using the delineation line as a guide while maintaining application of the suction. The patient's stomach is closed along a sealing line using the delineation line as a guide. In accordance with one preferred aspect of this method the application of regulated suction to the patient's stomach results in a suction force of 0.05 to 200 pounds within the patient's stomach. In accordance with another preferred aspect of this method the application of regulated suction to the patient's stomach applies a suction force per unit length within the patient's stomach at the location of the apertures, with the suction force per unit length being in a range of 0.02 to 21 pounds per inch.

DESCRIPTION OF THE DRAWING

FIG. 9 is an isometric view of a system constructed in accordance with another aspect of this invention, wherein the system includes a suction controller/indicator constructed in accordance with this invention for connection to a sizing device constructed in accordance with this invention;

FIG. 9A is an isometric view of another system constructed in accordance with this invention, wherein the system includes an alternative preferred suction controller or regulator;

FIG. 10 is an enlarged vertical sectional view of the suction controller/indicator shown in FIG. 9;

FIG. 10A is an enlarged vertical sectional view of the suction controller shown in FIG. 9A;

FIG. 11 is an enlarged elevation view of the distal end of an alternative preferred embodiment of a sizing device constructed in accordance with this invention;

FIG. 12 is an enlarged view of the distal portion of the sizing device shown within the circle identified by the letter "A" in FIG. 11;

FIG. 13A is a sectional view taken along line 13A-13A of FIG. 12; and

FIG. 13B is a sectional view taken along line 13B-13B of FIG. 12.

DETAILED DESCRIPTION OF THE PREFERRED EMBODIMENT

Figure 1:
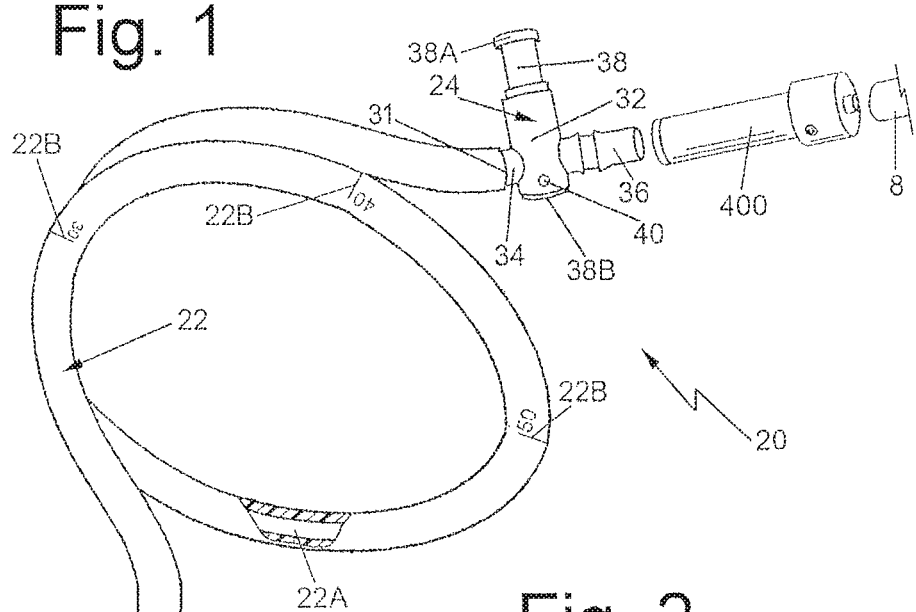
FIG. 1 is an isometric view of a portion of a system constructed in accordance with one exemplary preferred embodiment of this invention including a sizing instrument or device, e.g., a sizing tube, shown partially in section, for performing a bariatric procedure, e.g., a sleeve gastrectomy, on a patient, with the valve of the device shown in its closed or "off" position.

Referring now to the various figures of the drawing wherein like reference characters refer to like parts, there is shown in FIG. 1 one exemplary embodiment of a system 20 constructed in accordance with one exemplary preferred embodiment of this invention including a sizing device or instrument for performing a bariatric procedure on a patient. FIG. 11 shows an alternative sizing tube of another system of this invention. All of the systems of this invention are particularly suitable for use in bariatric metabolic surgeries, such as a sleeve gastrectomy. However, the systems and instruments of the subject invention are not limited to such usage. Thus, the systems and instruments of the subject invention can be used with other types of medical procedures where suction is to be applied to the stomach or a fluid introduced into the stomach The system 20 comprises a flexible sizing tube 22, a valve 24 and a perforated tip 26. In FIG. 11 there is shown an alternative and preferred sizing tube 122. In both embodiments the sizing tube 22 and 122 is an elongated flexible member having a central passageway 22A (FIGS. 1 and 3B) formed, e.g., extruded, of any suitable material. One particularly suitable material is a second generation styrenic block copolymer with a hydrogenated midblock of styrene-ethylene/butylene-styrene (SEBS) or styrene-ethylene/propylene-styrene (SEPS), such as sold by Kraton Performance Polymers, Inc. under the trade designation Kraton grade G2705.

The sizing tube 22 and 122 is somewhat long, e.g., approximately 76 cm, so that it can be extended through a patient's mouth into the patient's stomach and preferably comes in plural sizes, with the appropriate size being selected for the particular patient to form a desired size stomach. For example, the outside diameter of the sizing tube may be available in 32, 36 or 40 French sizes, while the inside diameter (i.e., the diameter of passageway 22A) is approximately 0.200 inch to 0.25 inch (depending on the outside diameter of the sizing tube). The sizing tube may include indicia or markings 22B at 30, 40 and 50 cm on its outer surface measured from its distal end to provide the user with information as to the depth that the sizing tube has been inserted into the patient's stomach. That indicia may be pieces of suture inserted into the wall of the sizing tube after it has been extruded. Alternatively, the indicia may be molded into the sizing tube (e.g., be in the form of a short section of suture molded into the material making up the sizing tube) or may be applied (e.g., printed) on the outside of the tube if suitable.

The perforated tip 26 of the sizing tube 22 and 122 is located at the distal end 28 and comprises a plurality of small apertures 30 extending through the side wall of the tube 22 and in fluid communication with the tube's central passageway 22A. The central passageway extends the entire length of the tube 22 and 122 from its proximal end 31, at which the valve 24 is located to the distal end 28 of the tip 26. As best seen in FIGS. 1, 11 and 12, the distal end 28 of the tip 26 is closed and is rounded, e.g., of hemispherical shape.

The valve 24 is in the form of a slide valve having a vent. The slide valve includes a body 32 having a first coupling 34 which is tubular and arranged to be disposed (e.g., frictionally fit) within the hollow proximal end 30 of the sizing tube 22. The body 32 includes a second coupling 36 which is also a tubular member. The two couplings 34 and 36 are axially aligned with each other and project radially outward from diametrically opposed locations on the body 32 of the valve. The body 32 is a hollow member in which a slide 38 is disposed.

The slide 38 is arranged to be slid into one of two positions to cause the valve 24 to be in either an open ("on") position or a closed ("off") position. To that end, the slide 38 is a hollow tubular member having a first end cap or head 38A at one end thereof and a second end cap or head 38B at the opposite end thereof and a pair of diametrically aligned openings (not shown) located in the side wall of the slide half way between the heads 38A and 38B. Each of the openings is of approximately the same internal diameter as the internal diameter of the couplings 34 and 36. When the slide 38 is in the position shown in FIG. 2 the valve is in its open or on position, whereupon the openings (not shown) in the slide 38 are aligned with the hollow interior of both of the couplings 34 and 36 thereby providing a fluid path therethrough. However, when the slide is in the position shown in FIG. 1 the valve is in its closed or off position, whereupon the openings (not shown) in the slide 38 are not aligned with the hollow interior of both of the couplings 34, so that respective portions of the side wall of the slide block the interior of the two couplings 34 and 36, thereby isolating the coupling from each other.

Figure 2:
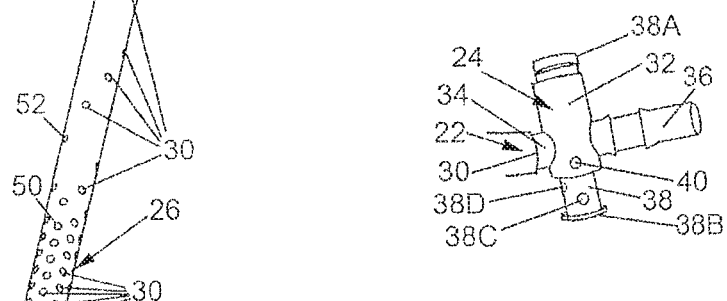
FIG. 2 is an isometric view of the valve shown in FIG. 1 in its open or "on" position.

As mentioned earlier the valve 24 includes a vent. To that end, the slide 38 includes a pair of apertures 38C and 38D (FIG. 2). Aperture 38C is disposed in the side wall of the slide 38 adjacent the cap 38B, whereas aperture 38D is disposed in the sidewall slightly inward of the aperture 38C and approximately 90 degrees from it. The body 32 includes an aperture 40. The aperture 40 along with aperture 38C serves as a vent for the valve when the valve is in its "off" or closed position. In particular, when the head 38B of the slide is pushed inward so that the slide is in the position like shown in FIG. 1, the aperture 38C of the slide will be aligned with the aperture 40 of the valve's body and the aperture 38D will be aligned with the hollow interior of the coupling 34. Accordingly, ambient air can flow through aligned apertures 40 and 38C into the interior of the slide and from there through aperture 38D into the interior of the coupling 34. Hence the interior of the sizing tube 22 will be at atmospheric or ambient conditions when the slide switch is in the closed or off position.

Figure 8:
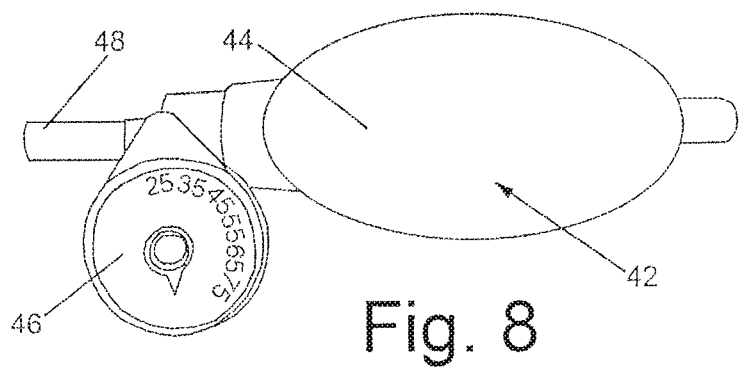
FIG. 8 is a plan view of a pumping device which is arranged to be used with the sizing device to pump a fluid, e.g., air, some other gas or liquid, into the stomach of the patient.

The coupling 36 is arranged to be selectively connected to a source of suction, e.g., a suction tube connected to a hospital's wall suction line (not shown), when suction is to be applied via the instrument to the stomach of the patient, or to a hand pump assembly 38 (FIG. 8), which will be described later, when a fluid, e.g., air, is to be applied into the patient's stomach. The coupling 36 is tubular and arranged to be disposed (e.g., frictionally fit) within either the hollow end of a suction tube connected to a source of suction or to a coupling (to be described later) forming a portion of the pump assembly 42 shown in FIG. 8. The source of suction may be a wall suction line that is typically provided in a hospital.

The pump assembly 42 is used to pump air or some other gas or liquid into the patient's stomach via the instrument 22 for reasons to be discussed later. The pump assembly 42 basically comprises a manually compressible bulb 44, an associated pressure indicator 46 or gauge and an adapter 48. The bulb 44 is arranged when squeezed to force any air within it out through an outlet port and into the adapter 48. The adapter 48 is arranged to be connected to the coupling 36 to releasably connect the pump assembly to the instrument 22. The bulb includes an inlet port through which air passes when the bulb is relaxed. The pressure gauge 46 is coupled to the outlet port of the bulb to provide an indication of the level of air pressure produced by squeezing the bulb. The pressure gauge typically indicates pressures in the range of 0-100 mmHg.

Figure 3A:
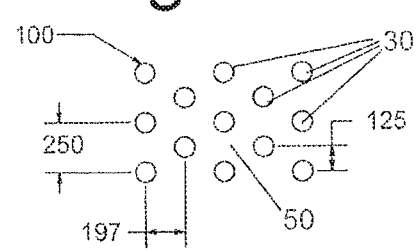
FIG. 3A is an enlarged plan view showing the spacing of a portion of the apertures located in the distal end of the device shown in FIG. 1.

The details of the apertures 30 will now be described with reference to FIGS. 1 and 3A. The apertures 30 are of a constant diameter along their entire length, are small in size and are arranged in a symmetrical array 50 about the periphery of the distal end portion of the sizing tube closest to the distal or free end 28. The spacing between the apertures 30 in the array portion 50 is shown in FIG. 3. However, in the area of the sizing tube 22 just proximally of the symmetric array 50, the apertures 30 are disposed in a helical or spiral configuration 52, with the spacing between adjacent apertures in the spiral configuration being greater than in the array 50, yet still equidistant. There are more apertures in the array area 50 to provide increased flexibility to the distal end of the sizing tube, so that it can be more easily directed to the appropriate location in the stomach. Typically this is done with laparoscopic graspers. In the area 52 the apertures are more spread out allowing suction to be applied at those portions of the tube. However, since they are spread out the tube is stiffer at this location. Having the tube be appropriately stiff is important because it has to be inserted in the patient's mouth adjacent a breathing tube, through the upper esophageal sphincter, through the esophagus and then through lower esophageal sphincter into the stomach.

It should be pointed out at this juncture that there are a sufficient number of apertures extending about the periphery of the sizing tube and along a substantial portion of the length of the sizing tube to ensure that when suction is applied the sizing tube is held in place by the suction and a clear line of delineation or demarcation of the sizing tube within the stomach is achieved (as will be described later).

The following constitutes various preferred exemplary diameters of the apertures 30. In particular, a preferred range of diameters for each aperture 30 is 0.05 inch to 0.25 inch, more preferred range of 0.030 to 0.200 inch, with the most preferred aperture diameter range being 0.07 inch to 0.15 inch. Thus, an embodiment of this invention can make use of apertures 30 of approximately 0.10 inch, whereupon the area of a single aperture is approximately 0.008 square inches.

Figure 3B:
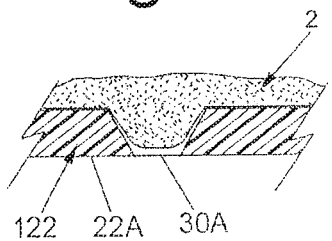
FIG. 3B is a cross sectional view of the shape of a typical preferred aperture, i.e., a flared aperture, for sizing instruments constructed in accordance with this invention.

It should be pointed out at this juncture that the apertures 30 need not be of a constant diameter. In fact, it may be desirable to make use of apertures that are flared so that the diameter of each of the apertures on the outer surface of the sizing tube is larger than the diameter of the apertures on the inner surface of the sizing tube. Such an arrangement is shown in FIG. 3B. The apertures 30A should facilitate the release of the sizing tube from the gastric tissue 2 when such action is desired since gastric tissue can more readily pull out of a flared hole 30A than a straight hole 30 or an inwardly tapered hole. For a 36 French sizing tube 122 the diameter at the outer end of each aperture 30A is approximately 0.11 inch, while the diameter at the inner end of each aperture 30A is approximately 0.08 inch and the thickness of the wall of the sizing tube is approximately 0.13 inch.

In the illustrated embodiment of FIG. 1 there are seventy-two apertures 30 in the first 2.5 inches of the length of the sizing tube 22, starting at its distal end, and sixteen apertures in the next 3.5 inches of the tube's length for a combined total of eighty-eight apertures. Another embodiment (FIG. 11) contemplated is a sizing tube including one hundred fifty-two apertures 30, each of a diameter of 0.10 inches and spread out uniformly in an array over the first five inches of the sizing tube's length.

In FIG. 11, an alternative sizing tube with a different configuration of aperture 30 is shown and will be described in detail later.

When a sizing tube constructed in accordance with any embodiment of this invention is in place in the stomach and suction applied, the applied suction creates a force that holds the sizing tube at that position. During laparoscopic surgery air pressure is used to inflate the abdominal cavity in order to provide an internal work space. Typically this air pressure is in the range of 0.1-0.4 psi. Suction applied to the sizing tube creates a negative pressure within the sizing tube and at the tube's apertures. The resulting force holds the sizing tube in place and anchors it to the stomach wall. This force is a function of: (1) the differential pressure between the abdominal cavity and the sizing tube and (2) the combined area of the apertures. For example, a sizing tube with eighty-eight apertures, each of a diameter 0.10 inches, equals an area of 0.7 square inches. With a positive pressure of 0.2 psi in the abdominal cavity and a negative pressure of 1.5 pounds (78 mm HG) in the sizing tube there is a differential pressure of 1.7 psi. The force is equal to 0.7 square inches×1.7 psi or 1.2 pounds. It is preferred that the force holding the sizing tube in position be in the range of 0.1 to 200 pounds, more preferably between 0.3 and 20 pounds and most preferably between 0.5 and 8 pounds.

The force applied to the stomach by the sizing tube with suction applied may also be considered independently of the positive pressure that is applied within the peritoneal cavity to facilitate laparoscopic surgery. As such, the suction force is the aperture area multiplied by the applied suction pressure. For example, if there are eighty-eight (88) apertures with a diameter of 0.1 inches, the aperture area is 0.7 square inches. With suction applied at a level of 2.4 psi (125 mmHg) the suction force applied by such a sizing tube is 0.7 square inches times 2.4 psi=1.7 pounds. That suction force is merely exemplary of many suction forces that are contemplated by the subject invention. To that end, a preferred range of suction force applied is 0.05 to 200 pounds, with a more preferred range being 0.1 to 100 pounds, and an even more preferred range being 0.3 to 20 pounds. The most preferred range is 0.5 to 8 pounds.

The suction force per unit length applied at the apertured portion of the device is another important parameter of the invention. For example, if there are one-hundred-fifty-two (152) apertures each with a diameter of 0.1 inches spread across a five (5) inch long longitudinal section of the sizing tube, the aperture area is 1.2 square inches. With suction applied at a level of 2.4 psi (125 mmHg) the suction force applied is 2.9 pounds. Thus the suction force per unit length applied at the apertured portion is 2.9 pounds divided by 5 inches or 0.58 pounds per inch length. That suction force per unit length is merely exemplary of many that are contemplated by the subject invention. To that end, a preferred range of suction force per unit length is 0.02 pounds per inch length to 21 pounds per inch length, with a more preferred range from 0.1 to 10 pounds per inch length, and with the most preferred range is from 0.2 to 5 pounds per inch.

As should be appreciated by those skilled in the art the distal end portion of the sizing tube 22 encompassing the array 50 of apertures will be subject to some degree of longitudinal collapse due to the multitude of apertures in that portion of the sizing tube. Thus, to prevent such collapse, which could be detrimental to the placement of the sizing tube within the patient's stomach, a helical anti-compression spring (not shown in FIG. 1 but shown in FIG. 11 and which will be described later) may be located within the distal end of the sizing tube in the area making up the array of apertures.

Turning now to FIGS. 4-7 the use of the systems of this invention will now be described. To that end, the distal end 28 of the sizing tube 22 or 122 is introduced through the patient's mouth and down through the patient's esophagus 10A into the interior of the patient's stomach 10B. The presence of the multiple apertures 30 in the distal end of the sizing tube renders that end quite flexible to facilitate the placement of it in the patient's stomach. If it is desired to "decompress" the patient's stomach (e.g. remove air from the stomach) or to remove any liquid from the stomach, the instrument 22 is attached via its coupling 36 to a suction line connected to a source of suction, e.g., a hospital wall suction line. The amount of suction provided may be controlled by use of the devices disclosed in U.S. Pat. Nos. 5,992,239 and 7,686,785, which are assigned to the same assignee as the subject invention and whose disclosures are incorporated by reference herein. The slide 38 of the valve 24 can then be moved to the open or on position. In particular, the user presses on the head 38A of the slide to move the slide to the position shown in FIG. 2, whereupon the ports in the side wall of the slide are aligned with the passageways through the couplings 34 and 36 so that suction will be applied down the interior of the sizing tube 22 and out through its apertures 30 to draw air and/or liquid out of the stomach through the instrument 22.

Figure 4:
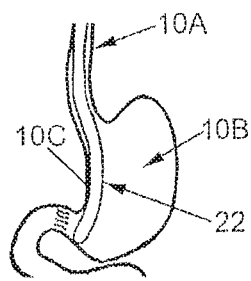
FIG. 4 is an illustration showing any of the sizing instruments of this invention being used to perform a sleeve gastrectomy, wherein the instrument is shown at its desired position within the stomach of the patient.
Figure 5:
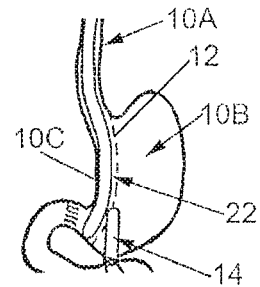
FIG. 5 is an illustration, similar to FIG. 4, but showing the stomach being resected by a conventional cutter/stapler device along a line parallel to the sizing device of this invention.

If after such decompression/stomach evacuation procedure has been accomplished (or if no such procedure has been accomplished), if it is desired to perform a sleeve gastrectomy procedure on the patient, the distal end of the instrument should be moved to the position shown in FIG. 4, if it is not already in that position. In that position the distal end of the instrument is located against the lesser curvature 10A of the stomach. If the valve 24 is not in the open position, its slide can be moved to that position to couple the source of suction to the sizing tube. The suction serves to hold the distal end of the instrument in position in the stomach and brings adjacent portions of the stomach into close engagement with the periphery of the distal end portion of the instrument. This action provides the surgeon with a clear line of delineation or demarcation of the instrument within the stomach, which can be readily seen by the surgeon via a laparoscope. In FIG. 5 this line of demarcation showing the position of the instrument in the stomach is represented by the broken line 12. The level of suction to be applied is typically in the range of 25-200 mm Hg, most preferably 50-150 mm Hg, but could be in the range of 1 mm Hg to 700 mm Hg.

Figure 6:
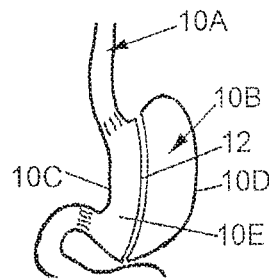
FIG. 6 is an illustration, similar to FIGS. 4 and 5, showing the stomach after a portion has been resected therefrom.
Figure 7:
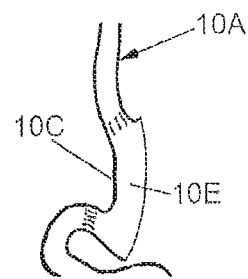
FIG. 7 is an illustration, similar to FIGS. 4-6, showing the residual portion of the patient's stomach after a portion has been resected therefrom and removed laparoscopically, thereby leaving the patient with a much smaller stomach.

The outer diameter of the instrument (sizing tube) used, e.g., whether 32, 36 or 40 French, is selected so that when the adjacent portions of the patient's stomach are brought into engagement with the distal end portion of instrument by the suction that distal portion of the instrument defines or establishes the size to which the patient's stomach is to be reduced. Accordingly, the surgeon can then use a conventional resecting stapler 14 or other conventional instrument to resect the stomach along, i.e., closely parallel to, the delineation line 12 to cut away a major portion 10D of the patient's stomach as shown in FIG. 6, with the marginal edges of the remaining stomach being stapled or otherwise joined along a seal line, thereby leaving the patient with a reduced size or residual stomach 10E as shown in FIG. 7.

In accordance with one preferred methodology of this invention, the seal line extends at least 0.5 cm (more preferably 1.0 cm) from said delineation line on the opposite side of the delineation line from the position of the sizing tube in the vicinity of the gastric esophageal junction (GEJ) and the Angle of HIS in order to minimize the chance of leakage along the seal line in that region. Thus, if the seal line is to be accomplished by use of a resecting stapler, the staple line should be laterally to the fat pad at the GEJ away from the delineation line to avoid stapling onto the GEJ and consequently prevent leaks.

Moreover, the seal line should not compromise the width of the residual portion of the patient's stomach (the "sleeve") near the incisura angularis. In this regard it is important that there is no further narrowing or obstruction of the gastric outlet or body of the stomach, since that action may result in or perpetuate a proximal staple line disruption. To that end, it is suggest to start 2 cm to 6 cm from the pyloris and to angle the stapler to prevent narrowing at the incisura angularis. In addition, it is suggested that the seal line be formed at least 0.5 (more preferably 1) cm from the delineation line on the opposite side of the delineation line from the position of the sizing tube in the vicinity of the incisura angularis to reduce the chance of the formation of a stricture thereat.

After the sizing procedure has been accomplished, the integrity of the patient's reduced size (residual) stomach 10E can then be checked for leaks. In particular, the suction tube from the source of suction may be disconnected from the coupling 36 while the valve 24 is in its open state or else the valve may be moved to the closed state by pushing on the cap 38B to the position shown in FIG. 1. In either case this action removes suction from the interior of the sizing tube and allows the sizing tube to vent, to enable any residual suction or pressure within the stomach to equilibrate to ambient atmospheric levels. The pump assembly 42 may then be connected to the instrument and the slide of the valve 24 moved to the open or on position, if it is not already in that position. At this point the user can manually squeeze the bulb 44 to force air from the bulb 44 into the instrument 20 down through the sizing tube 22 and out through the apertures 30, thereby insufflating the stomach to a desired pressure. That pressure is indicated on the pressure gauge 46. At the same time that the bulb is being squeezed to pressurize the stomach saline solution can be applied to the outer surface of the stomach along the suture/staple line. Thus, if there are any leaks, air bubbles will be produced at the site of the leak(s), which can be readily observed by the surgeon via the laparoscope. Alternatively, a leak test can be performed by merely opening the valve 24 and introducing a suitably colored liquid, e.g., saline solution with methylene blue dye, through the instrument into the stomach of the patient. Any leak will be readily observable via the laparoscope by the egress of blue dyed saline through the leak site(s).

During bariatric surgery it is necessary to mobilize the greater curvature of the stomach by separating it from the omentum and other parts of the anatomy where it is connected. This requires manipulation of the stomach and lifting the lesser curvature. After mobilization the stomach may be less spread out than before mobilization resulting in bunching and folding of the stomach. In such a case, once the sizing tube of this invention is in place and suction applied it may be difficult to determine exactly where the sizing tube is as the folds of the stomach might make it harder to discern the precise position of the sizing tube or if the fold(s) is/are large enough such fold(s) could appear to be the sizing tube itself. Accordingly, to overcome the problem of stomach bunching, should it occur during a sizing procedure, the application of suction, if applied, should be discontinued. Then air or saline should be introduced into the stomach via the sizing tube to expand the stomach and thereby "unfold" it. Once that has been accomplished the air or saline can then be removed by reapplying suction to thereby decompress the stomach and provide proper delineation of the sizing tube.

It should be pointed out at this juncture, that in lieu of the components described above, the system can be configured with the sizing tube, hand pump and suction connector and a selector valve all integral, allowing the user to select between the three functions of suction, inflation and vent.

Other sources of suction can be used in place of the suction source typically found in a hospital. For example it is contemplated that a system constructed in accordance with this invention may include a portable pump having a suction controller to be able to provide suction levels up to 700 mm Hg vacuum. In U.S. Pat. No. 7,857,806, whose disclosure is incorporated by reference herein, there is disclosed a portable pump which can be modified for use with the subject invention. In typical operation of a gastric sizing tube of this invention the level of suction applied is approximately 100 mm Hg vacuum. However, it is desirable to go as high as 700 mm Hg to increase securement force and delineation. This level of suction can be considered safe when it is only being applied for a short period of time. It is also desirable that the source of suction have good flow. In many cases, the lower esophageal sphincter and/or the upper esophageal sphincter seal around the gastric sizing tube. Sometimes, it is possible that a seal may not exist or be very good because the sphincters are relaxed or open. In such a scenario air would flow into the mouth and then into the sizing tube. A suction source with good flow capacity should overcome any such air leaks. It is believed that adequate flow output is at least 1 LPM at 100 mm Hg vacuum. A higher flow rate, e.g., 10 LPM at 100 Hg would likely be better.

It should be pointed out at this juncture that at the beginning of the sleeve gastrectomy procedure the sizing tube is placed in the stomach as described above. Some clinicians do this before establishing pneumoperitoneum and laparoscopic visualization, while others do this after establishing pneumoperitoneum and laparoscopic visualization. Once the sizing tube is placed in the stomach, suction is applied to decompress the stomach by removing air and liquid that is in the stomach. To that end, some clinicians like to move the sizing tube around to various parts of the stomach with suction applied in order to be certain that all stomach contents have been removed. After decompression of the stomach the sizing tube can be moved to the lesser curvature of the stomach and suction applied to secure the sizing tube in position and to create a visually perceptible line of demarcation, such as described previously. Prior to sizing and resecting the stomach there are a number of other preparatory surgical steps such as dissecting the greater curvature of the stomach from the omentum, dissecting and sealing the blood vessels of the greater curvature, etc. These steps are typically done after decompression of the stomach but before sizing of the stomach sleeve. They can be done with the sizing tube secured against the lesser curvature or with the sizing tube at another location within the stomach. Ultimately, prior to sizing and resecting the stomach the sizing is placed against the lesser curvature with suction applied to secure the device and provide the visually perceptible line of demarcation.

Using the visual demarcation line, the stomach can be resected with a cutting stapler that simultaneously seals and cuts the stomach into the correct shape. Typically the stapling follows the demarcation line and because the line of demarcation is clear the stapler can be positioned slightly away from the demarcation line, such as at the incisura anuglaris and the gastroesophageal junction, as described above. After the stomach has been sized, some surgeons perform a leak test, which can be performed as also described above.

Turning now to FIGS. 9 and 10, the details of an alternative system 120 will now be described. The system 120 makes use of a sizing tube or instrument 22 or 122 and valve 24 like those described above plus the addition of an integrated suction controller or regulator 200. In the interest of brevity the components and features of the system 120 that are the same as the system 20 will be given the same reference characters and the details of their construction, arrangement, function and operation will not be reiterated.

As can be seen in FIG. 9 the integral suction controller 200 is positioned between the sizing tube 22 (or 122, as the case may be) and the valve 24. Alternatively, it may be positioned connected to the valve, so that the order of components is as follows: sizing tube 22 (or 122), valve 24 and controller 200. The suction controller serves to ensure that a desired level of suction is applied to the sizing tube 22 (or 122) when the valve 24 is open to ensure proper and safe operation of the sizing tube. The suction controller 200 has a suction source side which is designated by the reference number 201 and is arranged to be connected to a source of suction such as a hospital's wall suction line, with the valve 24 interposed therebetween. The coupling 36 of the valve 24 is connected to a conduit or suction line 122 which is in turn connected to some source of suction (e.g., the hospital wall suction line—not shown). The opposite side of the controller 200 is designated by the reference number 202 and is arranged to be connected to the proximal end 31 of the sizing tube 22.

The controller 200 is housed within a hollow housing 203, which includes a cover 204. The housing and the cover are each formed of a rigid plastic, such as ABS. A piston 205 is disposed within the housing and is also formed of a rigid plastic, such as ABS. The piston includes a top portion 206 which extends through an opening 210 in the cover. The space between the outer periphery of the top portion 206 and the opening 210 forms a vent or port to the ambient atmosphere so that the chamber 213 will be at the pressure of the ambient atmosphere.

A spring 207 is located within the housing under the piston 205 and serves to bias the piston upward in the housing. The spring is formed of any suitable material, e.g., stainless steel. A rolling diaphragm 208 is coupled to the piston 205 and the housing 203. Diaphragm 208 is engaged in a sealing fashion between housing 203 and cover 204. The diaphragm can be formed of any suitable material, e.g., Nitrile. A seal 209 is located on the underside of the piston and is arranged to engage a seat 215 when excess suction is applied (as will be described later). The seal is formed of any suitable material, e.g., silicone rubber. The interior of the housing just below the cover 204 and above diaphragm 208 forms a first chamber 213, while the portion of the housing below the diaphragm forms a second chamber 214, with the diaphragm isolating the two chambers from each other. The seat extends about the periphery of the conduit 211.

Operation of the controller 200 is as follows. Suction is applied from the suction source (not shown) through the open valve 24 and into a conduit 211 at the suction side 201 of the controller and to the patient side 202 via the conduit 212. The proximal end 31 of the sizing tube 22 is connected to the conduit 212, so that suction is delivered to the sizing tube and subsequently to the patient. The controller 200 is configured to limit the amount of suction applied to the patient to a predetermined, desired level, even if a suction level greater than the predetermined level is applied via that conduit 211 from the suction source. The predetermined or desired suction level is established by the spring 207 and dimensions of the housing 203, the piston 205 and the seal 209. In this regard the pressure within chamber 213 will be equal to atmospheric pressure by virtue of the communication of the chamber 213 with the ambient atmosphere via the vent 210. With suction applied, the pressure differential between the chambers 213 and 214 forces the diaphragm 208 and the piston 205 downward toward the seat 215 of the housing 203 against the bias of the spring 207. If the suction applied via conduit 211 is greater that the predetermined level the piston 205 and diaphragm 208 will move such that the seal 209 on the bottom of the piston comes into engagement with the seat 215 thereby isolating chamber 214 from the vacuum source. This action thereby limits the level of suction in chamber 214 and ultimately at the patient to the predetermined level. If, however, the suction applied via conduit 211 is less than the predetermined level the piston 205 and diaphragm 208 will only move part of the way downward. As such the level of suction applied to conduit 211 will equal that in conduit 212 and that applied to the patient.

The controller 200 is arranged to provide an indication as to whether or not the suction applied is equal to or less than the predetermined, desired, level. Thus, the top surface of the portion 206 of the piston 205 is in the form of a colored tape 206A. The color of the tape is selected to provide a distinctive appearance from the rest of the piston, e.g., the periphery of the top portion 206. For example, in a preferred embodiment the tape 206A at the top portion 206 of the piston is colored white, while the remainder of at least the top portion 206 of the piston, if not the entire piston, is colored red. The cover 204 is preferably the same color as the tape 206A, e.g., white, or some other color that will readily contrast with the color of the top surface (i.e., the tape 206A) of the piston. The choice of a contrasting appearance, e.g., color, of the piston from the appearance of its tape top surface and the cover serves to facilitate visualization of the level of suction applied. For example, when the suction level in chamber 214 has not reached the predetermined, desired level the top portion 206 of the piston 205 will protrude above the top surface of the cover 204 and a red band (the periphery of the top portion 206) will be readily visible. When the level of suction in the chamber equals the predetermined set point (i.e., the desired level) the piston 205 will be at or below the surface of the cover 204 and the red band will not be clearly visible.

Turning now to FIGS. 9A and 10A there is shown an alternative suction controller or regulator 300 constructed in accordance with this invention and forming a portion of an alternative preferred system of this invention. The controller 300 is constructed similarly to the controller 200 except that it does not include any mechanism for indicating the level of suction applied. It does, however, include structure (to be described shortly) which ensures that the upper chamber 213 is always at atmospheric pressure. In addition, it includes means to prevent the piston 205 from becoming stuck for an extended period of time on the seat 215 in the event of what will be referred to hereinafter as an over-travel situation. Since many of the components of the controller 300 are also found in the controller 200, in the interest of brevity the common components of the controller 300 with the controller 200 will be given the same reference numbers and the details of the structure, arrangement and operation of those components will not be reiterated.

As can be seen in FIGS. 9A and 10A, the cover 204 includes a hole or port 302, which will be referred to as the atmospheric reference port. The port 302 extends through the thickness of the cover and is in fluid communication with the interior of upper chamber 213 to maintain that chamber at atmospheric pressure. Inasmuch as the port 302 is located in the top surface of the cover, it is susceptible to being blocked or covered by a sticker, some other object or even the finger of a user. To prevent such an occurrence the cover 204 includes structure to prevent blockage of the port 302. In particular, the cover 204 includes a thickened portion 304 located adjacent the port 302 with an elongated shallow slot 306 extending through the thickened portion 304. The outer or top end of the atmospheric reference port is located at the bottom of the slot 306 and is in fluid communication therewith. Each end of the slot is open. Thus if something should be on the top surface of the thickened portion 304 of the cover 204 disposed over the port 302 air can still enter into the port via either open end of the slot.

It has been determined that if the controller 300 is operated in a manner such that a high level of suction is applied very rapidly, the piston 305 may experience an over-travel wherein it moves downward very quickly such that the seal 209 on the underside of the piston becomes stuck on the seat 215. Under this condition the line 212 to the patient would have a higher level of vacuum than the controller was set to provide. The controller could stay in that state for an extended and indefinite period of time, particularly if the apertures 30A in the sizing tube 22 are blocked, e.g., are in tight engagement with the surrounding gastric tissue or are otherwise blocked. To prevent such an occurrence, the controller 300 includes two bleed holes. In particular, as can be seen in FIG. 10A the diaphragm 208 includes a bleed hole 308 in the central portion thereof. The piston 205 of this embodiment is somewhat different in construction than the piston 205 of the controller 200 in that it includes a hollow portion defined by a side wall 310. The sidewall 310 includes a bleed hole 312 extending radially therethrough. Thus, the interior of the hollow portion of the piston 205 is in fluid communication with the lower chamber 214 via bleed hole 312. Since the diaphragm 208 includes the bleed hole 308, which is in communication with the upper chamber 213, that chamber will be in fluid communication with the lower chamber via the bleed hole 308. Hence, if the piston should become stuck on the seat, air which enters into the upper chamber 213 via the port 302 can then pass through the bleed hole 308 into the interior of the piston and from there through the bleed hole 312 into the lower chamber 214. The ingress of air into the chamber 214 will decrease the vacuum within the chamber, thus enabling the spring 207 to move the piston 205 upward and off of the seat 215. In accordance with one exemplary preferred embodiment of the controller 300, the bleed hole 308 is approximately 0.1 inch in diameter, while the bleed hole 312 is approximately 0.015 inch in diameter. During typical operation the flow rate of air into chamber 214 via bleed hole 312 is in the range of 10 standard cubic feet per hour (SCFH) or lower.

As best seen in FIG. 10A the underside of the cover 204 includes a disk 314 located thereon. The disk 314 is formed of the same material as the material of the seal 209. The disk 314 serves to seal the diaphragm bleed hole 308 when the piston is in its maximum up position. The seal 314 serves to prevent the ingress of liquid into the upper chamber 213 when the system is being used to determine if the sealed residual portion of the patient's stomach has any leaks. In this regard, as discussed earlier a dyed liquid can be pumped into the patient's residual stomach via the sizing tube. If that procedure is accomplished using a system like the system shown in FIGS. 9A and 10A, the dyed liquid will be introduced into the chamber 214 and from there through line 212 to the sizing tube. Since the diaphragm 208 includes the bleed hole 308, the dyed liquid within the chamber could leak out of the chamber through the bleed hole into the upper chamber 213, but for the presence of the disk 314 preventing that from occurring.

It has been determined that when a gastric sizing tube, like that described above, is in the stomach of a patient, with suction applied, on some occasions the gastric tube may become clogged. In particular, it is suspected that mucosa from the stomach gets pulled into the apertures or perhaps there is some clotted blood in them. When the apertures are significantly clogged, the sizing tube appears to be stuck to the inside of the stomach, even when suction has been turned off and the sizing tube is vented. Such action is concerning if the withdrawal or removal of the "stuck" tube would damage the stomach by pulling on it. Using the bulb 44 to send air pressure into the sizing tube may unclog some of the holes and then air can enter the stomach. Pumping more air into the stomach expands the stomach, separating the inner lining of the stomach from the outside diameter of the tube. As such, the tube is then freed up for removal from the stomach. However, there are some situations in which the apertures cannot be unclogged by just squeezing the bulb as not enough pressure is generated even if the user squeezes really hard and multiple times.

One solution to this potential problem is the addition of at least one one-way valve at the distal portion of the sizing tube. An exemplary embodiment of a sizing tube incorporating a pair of such valves is shown in FIGS. 11 and 12, with each valve being designated by the reference number 122. The sizing tube 122 is similar to the sizing tube 22 described heretofore, except for the inclusion of the one-way valve(s), each of which is designated by the reference number 124, and a spring, which is designated by the reference number 126. In the interest of brevity the common features of the sizing tubes 22 and 122 will be given the same reference numbers and the details of their construction, arrangement and function will not be reiterated. To that end, as can be seen in FIGS. 11 and 12 the spring 126 is located within the distal end portion of the sizing tube 122 and extends from just distally of the distal-most apertures 30 to a point slightly proximally of the proximal-most apertures, e.g., approximately 1 to 1.5 inches beyond the proximal-most apertures. The spring 126 can be formed of any suitable material. One exemplary material is stainless steel 302. In that embodiment the free length of the spring is approximately 5.75±0.25 inches, with an outside diameter of approximately 0.215±0.10 inch, with closed ends, a wire diameter of 0.015 SS±0.001 inch, and with 8 active coils per inch ±1.

Each of the one-way valves 124 basically comprises a slit in the wall of the sizing tube 122. The slits are located proximally of the proximal-most apertures 30 so that they do not engage any of those apertures. The slits extend parallel to the longitudinal axis of the sizing tube and are disposed diametrically to each other. Each slit is approximately 0.440±0.60 inch in length, with the opposing edge portions of the sizing tube's sidewall contiguous with each slit being in engagement so that each slit is normally closed as a result of the resiliency of the material making up the sizing tube. In the exemplary embodiment shown the two one-way valves 124 are located in the area encompassed by the internal spring 126, which provides support to the sizing tube to prevent it from kinking or collapsing.

When suction is applied to the sizing tube the valves 124 are normally (automatically) closed. Upon the application of pressure, e.g., the introduction of a fluid, such as air or saline that is pumped into the sizing tube from the bulb 44, the slits open and the fluid is enabled to pass therethrough out of the sizing tube into the patient's stomach.

It should be pointed out at this juncture, that while the embodiment 122 makes use of two one-way valves 124, other arrangements are contemplated. Thus, the sizing tube can make use of only a single one-way valve or more than two one-way valves. Moreover, while each one-way valve being formed of a slit is preferred due to its simplicity other types of one-way valves can be used. For example, the one-way valve could be spring-loaded momentary valve.

Since the one-way valves 124 are configured so that they allow fluid to pass from inside the sizing tube to outside the sizing tube, but not the reverse, the valves do not pull anything in from the patient's stomach, so that they should not get clogged by materials getting sucked into the sizing tube during the application of suction. If the apertures 30 get clogged and the sizing tube gets "stuck" a fluid, e.g., air or saline, can be easily pumped from the bulb 44 into the sizing tube through the one-way valves, thereby expanding the stomach to free the sizing tube so that is no longer stuck. The one-way valves 124 can be operated to pump a fluid therethrough into the patient's stomach before or after the resection of the stomach, depending upon if and when the sizing tube becomes stuck. In fact, if during the bariatric procedure the stomach becomes folded with at least one fold to obscure or interfere with the visualization of a visually perceptible delineation line, the application of suction to the patient's stomach via the sizing tube can be halted, and a fluid, e.g., air or saline, pumped into the patient's stomach via the one-way valves to thereby remove the at least one fold, whereupon suction can be reapplied to the patient's stomach to hold those portions of the patient's stomach in such engagement with the sizing tube to thereby provide the visually perceptible delineation line used to resect the stomach.

Turning back to FIG. 1, it can be seen that the system 20 shown therein (or any system constructed in accordance with this invention for that matter), may include a flow meter 400 to monitor the flow of fluid through the system and thus enable one to infer the level of suction in the distal end of sizing tube. The flow meter 400 may be of any conventional construction, one particularly effective flow meter is that shown in U.S. Pat. No. 7,438,705 (Karpowicz et al.), which is assigned to the same assignee as the subject invention and whose disclosure is incorporated by reference herein. When using this flow meter it may be desirable to have a reservoir or fluid trap between the sizing tube and the flow meter, so that liquid from the stomach does not interfere with the operation of the flow meter.

As an alternative to use of a flow meter to determine the level of suction within the distal end of the sizing tube, the sizing tube may be constructed to include a passageway or lumen in communication with hollow passageway 22A at the distal end of the sizing tube. Such an arrangement is shown in FIG. 13A. In particular, a lumen 402 extends down through the passageway 22A of the sizing tube 122 the proximal end of the sizing tube to a position ending just before the distal end of the sizing tube. The lumen 402 is open at its distal end. Thus, one can measure the level of suction at the distal end of the sizing tube by coupling a suitable device at the proximal end of the lumen 402.

The lumen 402 can be used for another purpose, in lieu of or in addition to the purpose of determining the level of suction within the distal end portion of the sizing tube. In particular, the lumen 402 can be used to clear the hollow passageway 22A at the distal end of the sizing tube of any secretions, e.g., mucous, which may gain ingress into the sizing tube. That passageway may be connected to a receptacle (not shown) for the collection of such secretions.

A receptacle can also form a portion of any system of this invention to be used to collect any gastric fluids from the patient. In such a case, the receptacle will be coupled to the distal end portion of the sizing tube via any suitable means to enable any gastric fluids drawn into the sizing tube to be carried into the receptacle. That system may also include an overflow detector of any suitable construction to provide an indication that the amount of gastric fluid within receptacle has reached a predetermined threshold, e.g., is about to overflow, and/or to provide a signal to a controller stop to halt the operation of the sizing tube so that no further fluid is drawn into the receptacle until it can be emptied.

As should be appreciated by those skilled in the art, systems and instruments for use in bariatric surgery should provide one or more of the following functions, with the more functions provided the better. They should be constructed for enabling atraumatic insertion into the stomach with a reduced number of insertions and atraumatic removal, with a reduced number of removals. They should enable one to readily decompress the stomach by removing air and other materials. They should enable one to draw stomach tissue together and stabilize and secure the stomach tissue for resection. They should provide sufficient delineation of the stomach tissue to enable accurate resection of the tissue, and minimize risk of accidental stapling. They should enable ease of positioning about the lesser curvature of the stomach and also enable one to readily relieve suction periodically to release the stomach tissue for repositioning, if necessary. The suction applying apertures of such systems/instruments should be properly sized to minimize the amount of tissue being drawn into the apertures upon the application of suction. And, they should enable one to infuse fluids into the stomach for various purposes, e.g., leak testing.

The systems and instruments constructed in accordance with this invention meet all of those criteria. In particular, with respect to the matter of atraumatic insertion and removal, it is clear that the sizing tubes of this invention achieve that end by providing a radiused distal end or tip, with the material making up the sizing tube being soft and pliable, and with a smooth exterior surface to minimize friction. Moreover, the sizing tube is sufficiently stiff to enable pushing of it into place through the patient's body, e.g., its apertures are configured and arranged to maintain stiffness parallel to its longitudinal axis. The valve and the suction controller enable the ready application, control and removal of suction. The application of suction facilitates tissue delineation and/or fluid removal. When suction is not applied the sizing tube can readily deliver fluid.

With respect to the function of decompressing the stomach by removing air and other materials from it, the instruments of this invention achieve that end by virtue of the fact that the source of suction can be controlled, with a valve being provided for the application and removal/venting of suction, and with the sizing tube being resistant to longitudinal collapse. Moreover, the sizing tube's apertures are properly sized to maximize fluid and debris removal. For example, the apertures are confined to only the stomach area. Moreover, in one embodiment they exhibit a maximal open area to sizing element total area, e.g., the aggregate area of the apertures is at least 10% of the area of the portion of the sizing tube in which the apertures are located. The array of apertures can be made to extend for at least approximately 1 inches of the sizing tube measured parallel to the longitudinal axis of the sizing tube. Preferably the array extends for approximately 2-5 inches and can extend up to 10 inches. The array of apertures can comprise a first region of at least approximately 2 inches in length measured along the longitudinal axis and wherein the aggregate area of the apertures in the first region is at least 10% of the area of the first region. In addition, the array of apertures can comprise a second region of at least approximately 3 inches in length measured along the longitudinal axis and located proximally of the first region, wherein the aggregate area of the apertures in the second region is at least 2% of the area of the second region. The sizing tube can have an outside diameter of at least 0.375 inch and can be in 32, 36 and 40 French sizes.

With respect to the function of drawing the stomach tissue together and into engagement with the sizing tube to stabilize and secure the stomach tissue for resection, the instruments of this invention achieve that end by virtue of the fact that the apertures are properly sized to minimize tissue trauma, are only in the stomach area, and the suction is controlled. Moreover the instruments include a valve for the application and removal/venting of suction. Moreover, the sizing tubes provide sufficient flow to overcome leaks around the esophageal sphincters and are resistant to longitudinal collapse.

With respect to the function of delineating the sizing tube in the stomach tissue to enable more accurate resection of the tissue and minimize risk of stapling of the sizing tube, the instruments of this invention achieve that end by having apertures of the sizing tube that are properly sized, confining them to the stomach area and having them extend along and about a sufficient length of the sizing tube to ensure than when suction is applied the sizing tube is held securely in place. Moreover, the apertures can be arranged in arrays that are uniform, circumferential and patterned for optimal suction application to draw stomach tissue together and hold the sizing tube in place. The controlled source of suction with sufficient flow acts to overcome leaks around upper and lower gastric sphincters. In addition, the valve serves to enable the application and removal/venting of suction. Relief of suction periodically facilitates the release the tissue for ease in repositioning.

With respect to the function of facilitating the infusion of fluids for various purposes, such as leak testing and unfolding, the instruments of this invention achieve that end by confining the apertures to the stomach area and providing a valve for the delivery of such fluids With respect to the function of enabling ease of positioning about the lesser curvature of the stomach, the instruments of this invention achieve that end by having their apertures patterned and with a density to facilitate flexibility perpendicular to the longitudinal axis of the sizing tube. If desired, a spring may be included in the sizing tube (such as described above) to facilitate flexibility perpendicular to the longitudinal axis of the sizing tube while at the same time preventing longitudinal conduit collapse due to perpendicular flexion. Such action enables the application of uninterrupted suction, or delivery of fluids.

With respect to the function of enabling atraumatic removal and reducing number of removals necessary, the instruments of this invention achieve that end by providing a valve removal/venting of suction and release of tissue. In addition, the apertures are properly sized to minimize tissue being drawn into them and the sizing tube is smooth for minimal friction on tissue.

Systems and instruments that are constructed in accordance with this invention should provide a means to reduce or otherwise solve leakage issues inherent in a sleeve gastrectomy or other a stomach resection procedures. In particular, it is believed that the instruments of the subject invention enable the applied suction to approximate the gastric tissues prior to staple clamping, thus enabling more effective "stress relaxation" of the compressed tissue. Moreover, it is believed that the subject invention reduces need for excess movement of the tissues/repositioning of the stapler. Once the surgeon has properly aligned the instrument with the lesser curvature of the patient's stomach, and the anesthesiologist has applied suction, the suction causes the gastric tissues to wrap around and cling tightly to the sizing tube nearest the lesser curvature, while effectively decompressing and emptying the stomach. The suction enables this positioning to be maintained throughout mobilization of the stomach, inspection of the anterior and posterior aspects of the stomach, as well as during stapler positioning, compression, firing, and removal. Due to this maintenance of positioning, the surgeon is no longer required to constantly pull on, or adjust the gastric tissue around a bougie or within the jaws of the stapler as has characterized the prior art, in order to keep the anterior and posterior aspects aligned properly, to locate the bougie, or ensure adequate compression of the tissue. Reducing the need to pull on and move the gastric tissues reduces the risk of gastric puncture, formation of scar tissue, technical error. Moreover, it may also reduce post-operative gastric inflammation, all of which may otherwise lead to gastric leaks. Reducing the pulling on the tissue may also enable fluid dispersion out of the compressed tissue to be more consistent and regular, resulting in the formation of a more secure seal, e.g., staple, line, and reducing the risk of leaks.

Another advantage of the subject invention is that it should act to prevent stretching of the gastric tissues during and after the procedure. In particular, with the gastric tissues tightly wrapped around the circumference of a sizing tube instrument constructed in accordance with this invention, the gastric tissues should not slide around the instrument. This gives the surgeon confidence in the alignment of the posterior and anterior portions of the stomach along the lateral side of the sizing tube, without excess pulling on the greater curvature of the patient's stomach. This reduced need to pull on the gastric tissues should result in tissue that is less taut and less stressed than can result from prior art techniques. Therefore, the tissue meets with lower-stress compression, resulting in less stress on the staple line, thus reducing the chance of leaks. Reduced stretching of the tissues also reduces the likelihood of technical errors, which may cause a stricture due to uneven stretching of the gastric tissue. As increases in intra-lumenal pressure, and stricture is often associated with leak, the reduction of strictures should also result in a reduction of leaks.

Still another advantage of the subject invention is that the suction produced by the sizing tube clarifies proper staple positioning, thus enabling a more accurate sleeve gastrectomy procedure. In this regard, with the application of suction, the gastric tissue wraps around and clings to the sizing tube. This action causes the remainder of the stomach to lie fairly flat, with a distinct delineation or demarcation line resulting along the lateral side of the sizing tube and marking the outside of the sizing tube. This easily visibly perceived delineation or demarcation line can thus be used as a clear guide for the stapler to follow, enabling a smooth, even staple line closely approximating the sizing tube's calibrated size. A clearly visible line of demarcation also helps to preclude inadvertent stapling of the sizing device such as was common with prior art devices due to an inability to determine the exact location of the devices within the stomach. Following the delineation line, with minimal required tissue manipulation may reduce the amount of staple overlap/crossing, which could otherwise contribute to leaks. The readily visually perceivable delineation line formed by the instrument of this invention is particularly useful for sealing the stomach in the vicinity of the gastro-esophogeal junction GEJ. In particular, the delineation line merges with the outside of the esophagus at the GEJ, enabling a clear identification of the GEJ, and Angle of HIS. This clarity of GEJ identification allows the surgeon to more accurately staple the remaining portion of the stomach without fear of stapling the weaker esophageal tissue.

It must be pointed out at this juncture that the various components of the instruments shown and described above are merely exemplary of various components that may be used in accordance with this invention to provide the capabilities as discussed above.

Without further elaboration the foregoing will so fully illustrate our invention that others may, by applying current or future knowledge, adopt the same for use under various conditions of service.

We claim:

1. A system for sizing the stomach of a patient for a bariatric procedure, said system comprising:
   a suction controller configured for producing controlled suction from a source of suction;
   a non-expandable instrument configured to be coupled to said suction controller, said instrument being a single elongated member forming a sizing tube formed of a flexible non-expandable material having a predetermined outside diameter configured for introduction through the esophagus into the stomach of the patient so that a portion of said sizing tube is disposed along the lesser curvature of the patient's stomach, said sizing tube having a longitudinal axis, a hollow interior defining a passageway, a proximal end portion, a tip having a distal end that is unencumbered, and a plurality of apertures disposed about the periphery of said distal end portion, said plurality of apertures being directed in a plurality of different radial directions from said longitudinal axis and being in fluid communication with said passageway, plural ones of said apertures extending along a portion of the lesser curvature of the patient's stomach when said sizing tube is located within the patient's stomach, whereupon controlled suction is applied to the hollow interior of said sizing tube and through said apertures to pull the lesser curvature of the patient's stomach into engagement with a portion of said sizing tube and contemporaneously therewith to pull other portions of the patient's stomach adjacent to said sizing tube towards portions of said sizing tube not facing the lesser curvature of the patient's stomach to anchor said sizing tube in place without the use of any expandable member to hold said sizing tube in place and to produce a suction-created visually perceptible delineation line on the exterior of the patient's stomach along a portion of the periphery of said sizing tube facing the greater curvature of the patient's stomach to serve as a guide enabling the patient's stomach to be sized along said suction-created visually perceptible delineation line and with said controlled suction as applied by said apertures serving as the sole means anchoring said sizing tube in place;
   wherein said suction controller is configured to apply controlled suction to said hollow interior of said sizing tube to result in a force in a range of 0.05 to 200 pounds anchoring said sizing tube in position within the patient's stomach;
   wherein said sizing tube is configured to apply a suction force per unit length within the patient's stomach at the location of said apertures when said controlled suction is applied to said sizing tube, whereupon the suction force applied per unit length is in a range of 0.02 to 21 pounds per inch based upon an aperture area of 1.2 square inches.

2. The system of claim 1 wherein said sidewall of said sizing tube includes at least one one-way valve, said at least one one-way valve being automatically closed when suction is applied to said interior of said sizing tube, said at least one one-way valve being openable to enable a fluid to be passed therethrough from the interior of said sizing tube into the stomach of the patient to prevent said sizing tube from becoming stuck in the patient's stomach.

3. The system of claim 2 wherein said at least one one-way valve comprises a slit in said sidewall.

4. The system of claim 3 wherein said slit extends parallel to said longitudinal axis.

5. The system of claim 1 wherein said controller comprises a spring-biased piston against a diaphragm arranged to be moved in response to the level of suction established by said suction controller, said diaphragm establishing at least one chamber.

6. The system of claim 5 wherein said system additionally comprises a passageway to enable a small amount of air from the ambient atmosphere to enter into said at least one chamber, said passageway being arranged to enable said small amount of air to enter into said at least one chamber even if all of said apertures are blocked.

7. The system of claim 6 wherein said at least one chamber is arranged to receive a fluid therein for introduction into the patient's stomach to provide an indication of a leak in the patient's stomach, and wherein said passageway is arranged for said small amount of air to pass therethrough from the ambient atmosphere but not for fluids to pass from said at least one chamber to the ambient atmosphere.

8. The system of claim 1 wherein said sizing tube is configured to permit flexing of thereof perpendicular to said longitudinal axis while preventing longitudinal collapse thereof due to perpendicular flexion.

9. The system of claim 8 additionally comprising a spring located in said tip of said sizing tube, said spring being configured to permit flexing of said sizing tube perpendicular to said longitudinal axis while preventing longitudinal collapse of said sizing tuber due to perpendicular flexion.

10. The system of claim 1 wherein an aggregate area of said plurality of apertures is at least 10% of the area of said sizing tube in which said plurality of apertures is located.

11. The system of claim 1 wherein said sizing tube has an outside diameter of at least 0.375 inch.

12. The system of claim 10 wherein said array of apertures comprises a first region of at least approximately 2 inches in length measured along said longitudinal axis and wherein an aggregate area of said apertures in said first region is at least 10% of an area of said first region.

13. The system of claim 12 wherein said array of apertures comprises a second region of at least approximately 3 inches in length measured along said longitudinal axis and located proximally of said first region, wherein an aggregate area of said apertures in said second region is at least 2% of an area of said second region.

14. The system of claim 1 additionally comprising a flow meter arranged to be coupled to said proximal end portion of said sizing tube.

\* \* \* \* \*